Figure 1:
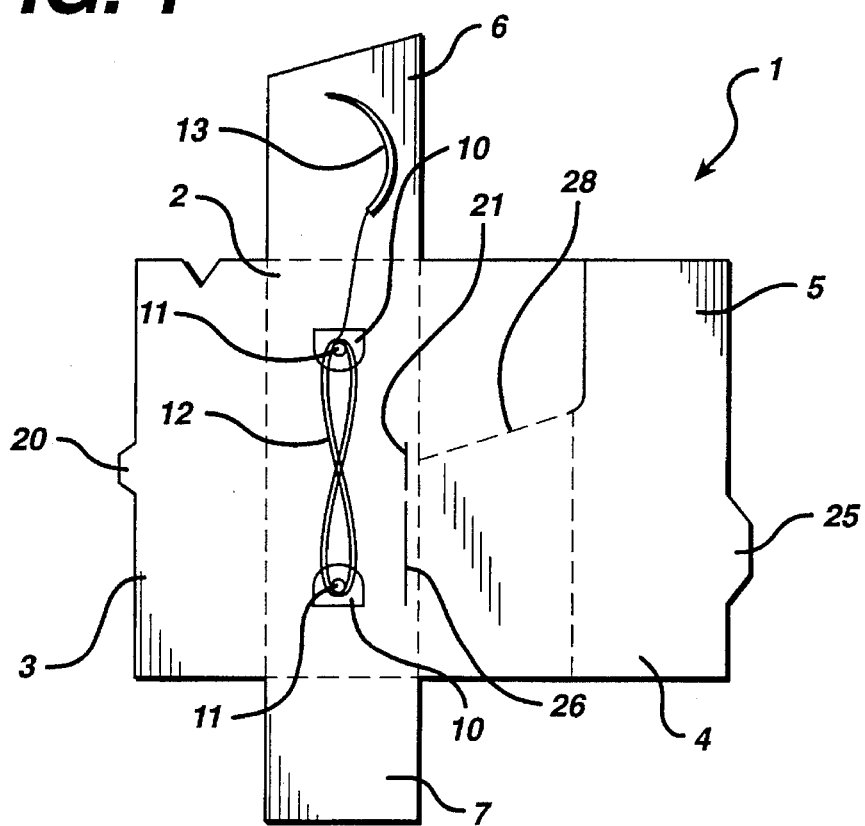

United States Patent [19]
Bordighon et al.

[11] Patent Number: 5,533,611
[45] Date of Patent: Jul. 9, 1996

[54] FOLDING PACKAGE FOR SURGICAL PRODUCTS

[75] Inventors: Marcos A. Bordighon, Centro; Jose L. L. Januzelli, Sao Dimas, both of Brazil

[73] Assignee: Ethicon, Inc., Somerville, N.J.

[21] Appl. No.: 238,554

[22] Filed: May 5, 1994

[30] Foreign Application Priority Data

May 5, 1993 [BR] Brazil ................................. 19301757

[51] Int. Cl.⁶ ................................................. A61B 17/04
[52] U.S. Cl. ........................... 206/63.3; 206/227; 206/388
[58] Field of Search ................................. 206/63.3, 227, 206/380, 388

[56] References Cited

U.S. PATENT DOCUMENTS

| | | | |
|---|---|---|---|
| 3,206,018 | 9/1965 | Lewis et al. | 206/63.3 |
| 4,120,395 | 10/1978 | Mandel et al. | 206/63.3 |
| 4,249,656 | 2/1981 | Cerwin et al. | 206/380 |
| 4,391,365 | 7/1983 | Batchelor | 206/380 |
| 4,572,363 | 2/1986 | Alpern | 206/63.3 |
| 4,700,833 | 10/1987 | Smith | 206/63.3 |
| 5,271,494 | 12/1993 | Odermatt et al. | 206/63.3 |
| 5,279,411 | 1/1994 | Brunken | 206/63.3 |

*Primary Examiner*—Jimmy G. Foster
*Attorney, Agent, or Firm*—Emil Richard Skula

[57] ABSTRACT

The present invention refers to a package (100,200) made up of a plurality of folding panels (101–106), particularly suitable for retaining a surgical suture (115) wound in a non-crossed manner on pins (111) that penetrate a first retaining panel (101) and are preferably arranged along semicircular paths. Thus, even a suture (115) made of a material provided with a great elastic memory can be retained in the package (100,200) of this invention for long periods of time, without assuming an accentuated undulated shape after being taken out of the package (100,200). Further according to the present invention, the package (100,200) includes a locking device of the tongue-slot type (130,131) for keeping the package (100,200) folded and closed, the respective slot (131) being disposed in a transversely median position in said first retaining panel (101).

6 Claims, 3 Drawing Sheets

FOLDING PACKAGE FOR SURGICAL PRODUCTS

The present invention refers to a folding package or retainer for surgical products, and more specifically to a package made up of a plurality of folding panels, particularly suitable for retaining sterilized surgical suture made of a polymeric material provided with an elastic memory, having one or more needles fixed at its ends.

Some types of package for surgical sutures are already known from the prior art, which vary according to the nature and purpose of the suture. In general, the main function of these packages is to protect the suture and the respective needle(s) during transportation, handling and storage until it reaches the final user. Besides, the most improved packages of the prior art have a reduced manufacture cost and their structural conception facilitates the opening, permitting that the suture-needle assembly be promptly reached and taken out of the package for utilization.

The prior art most pertinent to the present invention is that described in the Brazilian Patent PI 8201615, filed by Johnson & Johnson, the contents of which is incorporated herein as a reference.

This patent refers to a folding package or retainer for a surgical suture with needles that include first and second panels for retaining surgical products, foldingly connected to each other, and first and second locking panels also foldingly connected to each other, the first locking panel being foldingly connected to the first retaining panel. All of these panels are rectangular, usually made of cardboard and connected to other by their longer, longitudinal edges, the final configuration of the retainer or package being obtained when the retaining panels are folded over each other with the suture between them, and the locking panels are successively folded in order to involve the retaining panels altogether.

The package of the prior art preferably comprises two locking devices of the tongue-slot type: one being capable of keeping the retaining panels folded over each other in order to stabilize the suture, the tongue of which is disposed at the free longitudinal edge of the second retaining panel and the slot of which being positioned on the first retaining panel, parallel and adjacent to the edge joining this panel with the first locking panel.

The second locking device permits fixing the second locking panel on the back face of the first retaining panel, in order to keep the package closed, and is made up of a tongue arranged at the free longitudinal edge of the second locking panel, which cooperates with a slot also arranged on the first retaining panel, this slot being adjacent and parallel to the slot of the first locking device.

The package described in Patent PI 8201615 is configurated in such a way that the respective suture can be reached and taken out of the package by the user through partial tear of the first locking panel. Besides, the corresponding needle is maintained in a compartment separate from the suture, whereby it is prevented from cutting the latter accidentally and possible damages to the sharp edges of the needle are avoided.

However, in view of the nature and the position of the second locking device described above, the prior art teaches that the suture should be wound in a crossed way, like an "8" in order not to be unduly withdrawn by the second locking device when it is taken out of the package. Since all the sutures have a certain degree of elastic memory, the ones that are wound in a crossed way for some time in the prior art have a great tendency to dispose themselves, after they have been withdrawn from the package, not in a rectilinear manner, as would be desirable, but rather in an accentuated undulated manner, which makes the practical use of the suture extremely difficult.

Although these problems occur with sutures made of the most different materials, even those of animal origin (for example, "cat gut"), the above-mentioned tendency to assume an undulated shape will be stronger with sutures made of a mutifilamentary or monofilamentary synthetic material, whose degree of elastic memory is higher. Monofilamentary sutures made of polymers have a specially great elastic memory.

Thus, one of the objectives of the present invention is to provide a folding package containing a filamentary surgical product, such as for instance a suture, wound in such a way that its shape, after it has been taken out of said package, will be as rectilinear as possible.

Another objective of this invention is to provide a package for surgical sutures, made of panels foldingly fixed to each other and configured in such a way that the removal of the suture will be effected without any possibility of undue retention by panel-locking device, independently of the manner in which the suture is wound.

The above objectives are achieved, according to a first feature of this invention, through a folding package for surgical products, particularly adapted for retaining a filamentary surgical product, characterized by comprising first and second elongated retaining panels foldably joined together by their longitudinal edges, the filamentary surgical product being wound in a non-crossed manner over the first retaining panel; a first auxiliary retaining panel foldingly joined to a transverse edge of the first retaining panel; and a first elongated locking panel, the longitudinal edge of which is foldingly joined to the longitudinal edge of the first retaining panel opposite the second retaining panel, the first locking panel having a substantially transverse weakened line.

A second feature of the present invention is a folding package for surgical products, particularly adapted for retaining a filamentary surgical product, characterized by comprising first and second retaining panels foldingly joined to each other by their edges, the filamentary surgical product being wound in a non-crossed manner over the first retaining panel; a first locking panel, the edge of which is foldingly joined to the edge of the first retaining panel opposite the second retaining panel; and a locking device of the tongue-slot type, the respective slot being disposed in a transversely median position of the first retaining panel.

According to a third feature of this invention, a folding package is provided for surgical products, particularly adapted for retaining a filamentary surgical product and characterized by comprising first and second retaining panels foldingly joined to each other by their edges, the first retaining panel having bores arranged along substantially semicircular paths, through which pins can pass to facilitate the winding of the filamentary surgical product in a non-crossed manner.

Figure 7:
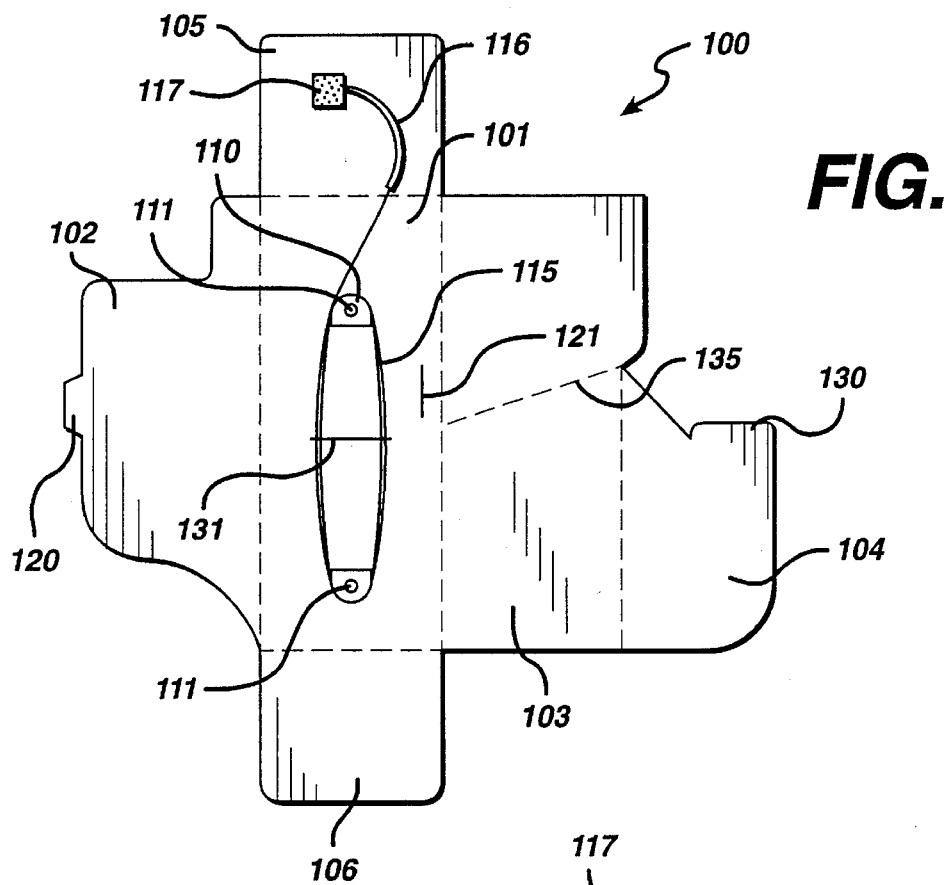
Figure 8:
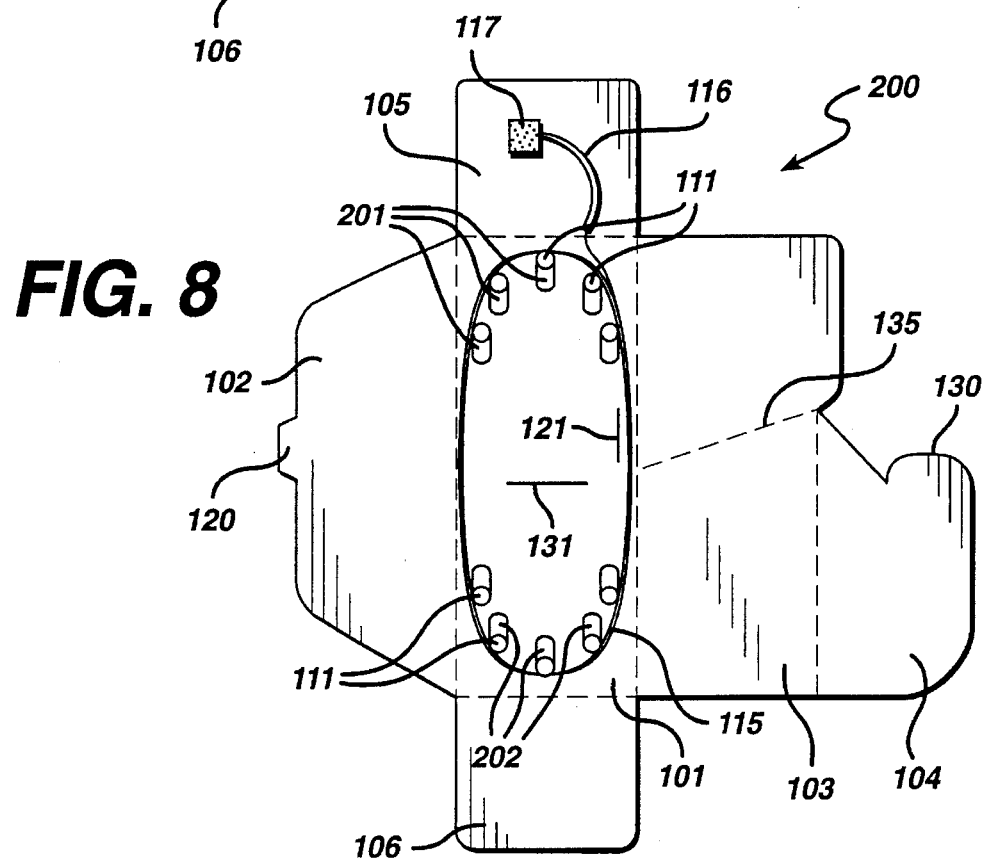

The present invention will now be described in greater detail with reference to the accompanying drawings, in which:

FIG. 1 schematically illustrates a folding package for surgical sutures as taught by the prior art most pertinent to the present invention, when open, that is to say, unfolded and disposed in a planar manner;

FIGS. 2 through 6 schematically show the successive steps of unfolding the panels that make up the package illustrated in FIG. 1;

FIG. 7 illustrates a first embodiment of the folding package for surgical products of this invention, when open, i.e. unfolded and disposed in a planar manner. This embodiment is particularly suitable for storing surgical sutures provided with a high degree of elastic memory; and FIG. 8 illustrates a second embodiment of the folding package for surgical products of this invention, also when open. This embodiment is suitable for retaining surgical sutures with any degree of elastic memory, preferably multifilamentary sutures.

With reference to FIG. 1, the folding package 1 of the prior art basically comprises a first rectangular retaining panel 2 connected respectively and foldingly by its longer longitudinal edges to a second retaining panel 3 and to a first locking panel 4, both rectangular too. This first locking panel 4 is also connected foldingly always by its longitudinal edge to a second rectangular locking panel 5.

Package 1 usually has further first and second auxiliary retaining panels 6, 7, approximately square and connected respectively and foldingly to the shorter transverse edges of the first retaining panel 2.

The first retaining panel 2 has two bores 10, disposed along the longitudinal symmetry axis of the former, through which respective pins 11 are introduced to facilitate the manual winding of a suture 12 having a needle 13 secured to one of its ends.

Suture 12 is generally made of a monofilamentary or woven multifilamentary polymeric material, and so it is provided with an elastic memory. Thus, when suture 12 is released, it tends to dispose itself in the configuration which it has presented before. In this way, accordingly to the prior art, the winding of suture 12 should be made in a crossed "8-shaped" manner, for reasons already mentioned that will be described in greater detail.

After this step of manual winding, pins 11 are withdrawn from bores 10 and suture 12 is kept on the first retaining panel 2, while suture 13 is disposed on the first auxiliary retaining panel 6 in the beginning of the steps of folding and closing package 1, which will now be described with reference to FIGS. 2 through 6.

Also two locking devices of the tongue-slot type are provided, which keep package 1 closed after panels 2–7 have been folded.

The first of these devices is made up of a first tongue 20, provided at the free longitudinal edge of the second retaining panel 3, and a first slot 21 disposed in the first retaining panel 2, in a position parallel to and adjacent to the longitudinal edge that joins that panel 2 with the first locking panel 4.

The second locking device comprises a second tongue 25, located at the free edge of the second locking panel 5, which cooperates with a second slot 26, also provided in the first retaining panel 2, in a position parallel to and adjacent to the first slot 21.

Panels 2–7, which for package 1, are made, as a rule, of cardboard of any area weight, but they can be made of plastic films or any other flexible material.

Figure 2:
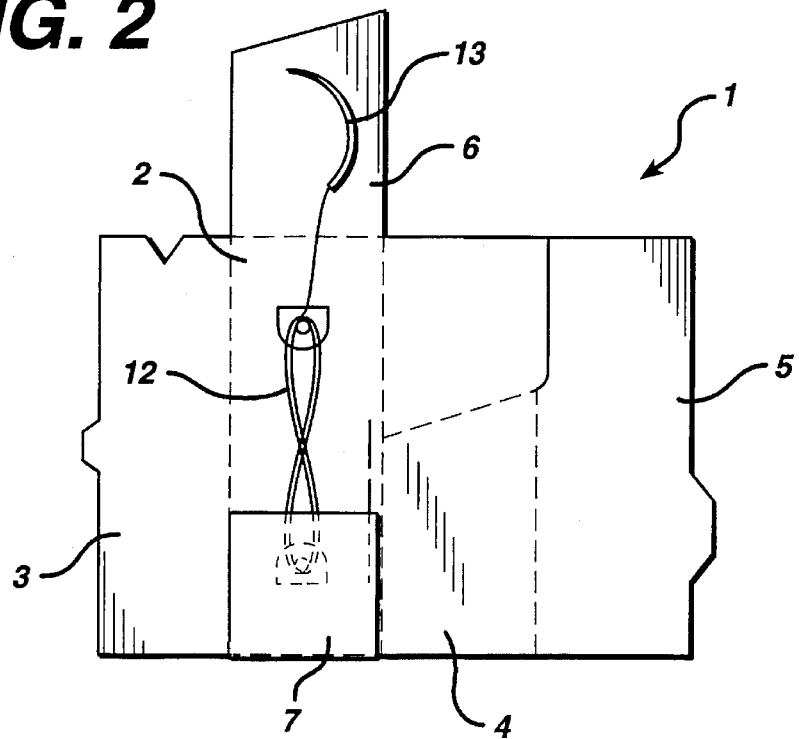
Figure 3:
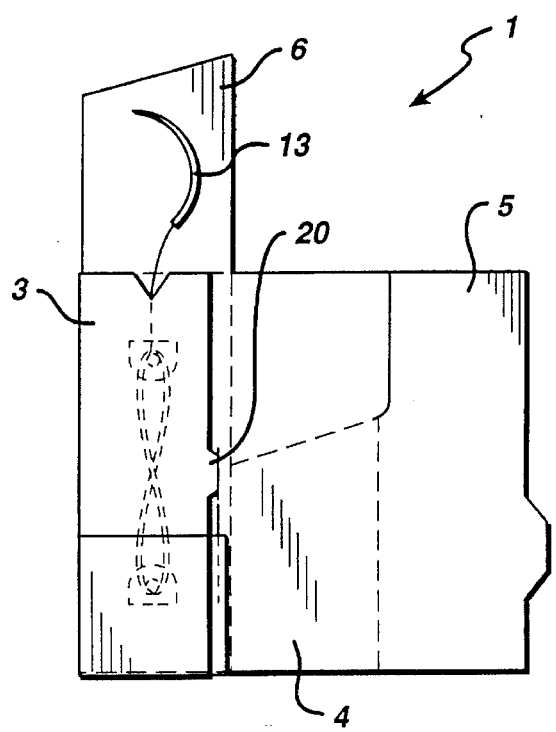
Figure 4:
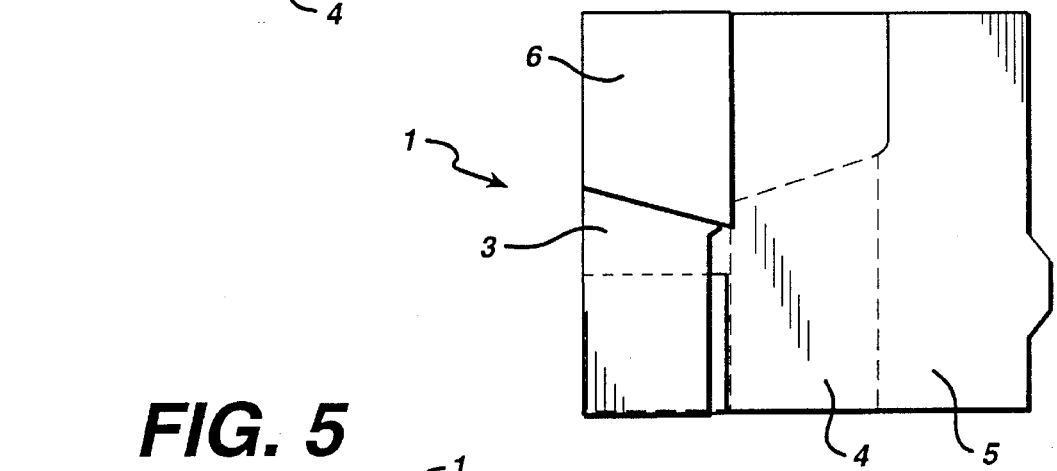

FIGS. 2–6 show the successive steps of folding and closing package 1. First, as illustrated in FIG. 2, the second auxiliary retaining panel 7 is folded over suture 12 and the first retaining panel 2, the second retaining panel 3 being then folded over suture 12, and first retaining panel 2 and the second auxiliary retaining panel 7, as illustrated in FIG. 3. Such panels 2, 3 and 7 are maintained in this position after the first tongue 20 has been inserted into the first slot 21.

Figure 5:
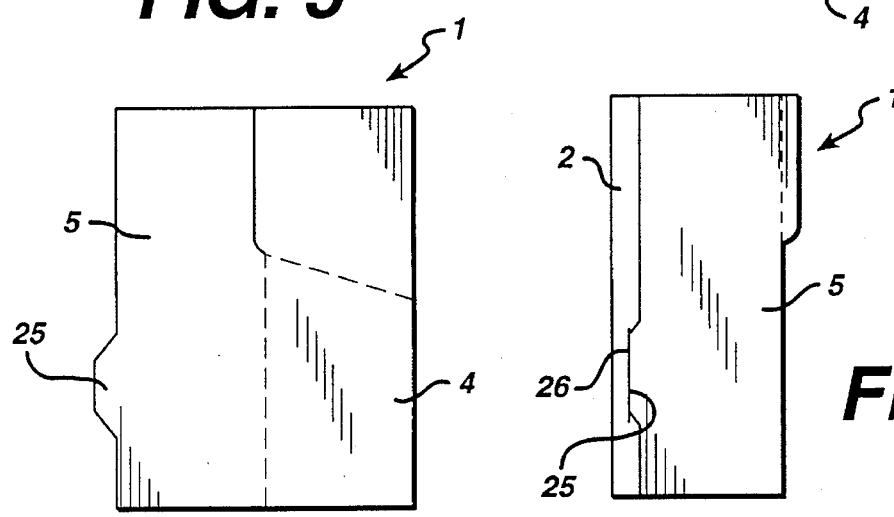
Figure 6:
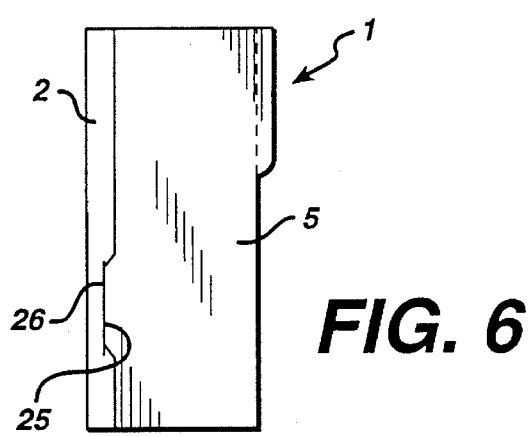

The first locking panel 6 is then folded over the second retaining panel 3, with needle 13 and a portion of suture 12 between them (FIG. 4), and first and second locking panels 4, 5 are successively folded over the other panels, so that the second tongue 25 is finally inserted into the second slot 26 from behind the first retaining panel 2, completing the assembly of package 1 (FIGS. 5 and 6).

Needle 13 enclosed in package 1 closed as described above is kept in a compartment separate from suture 12 and is easily accessible, since a portion of the first locking panel 4 can be raised after tearing a weakened line 28, allowing the first auxiliary retaining panel 6 to be raised as well, in order to exhibit needle 13 and allow a user to hold it either by hand or with a nipper and pull it to withdraw the whole suture 12 out of package 1.

As already mentioned, any sutures and especially the monofilamentary ones made of a polymeric material have an elastic memory. So, the turns of a wound suture around pins 11 tend to expand in a continuous manner, that is to say, in the direction of the edges of the first retaining panel 2, thereby creating the great risk of the second tongue 25 catching one or more of these turns when it is inserted into the second slot 26, in which case suture 12 will undergo unwanted retentions while being pulled out of package 1. Such retentions may have disastrous consequences if they occur during a delicate surgical procedure.

In view of this tendency to centrifugal expansion and the positioning of the first tongue 25 and of the second slot 26 in package 1, made in accordance with the teaching of the prior art, suture 12 must be wound in a crossed manner, forming an "8" in order to reduce centrifugal expansion of the turns of suture 12 to a minimum, preventing it from being retained by the second tongue 25 when the later is inserted into the second slot 26.

However, sutures 12 enclosed in package 1 of the above-described type will remain wound in an "8" shape for relatively long periods, until they are finally taken out of the respective packages 1 for use.

For this reason, the already mentioned elastic memory of suture 12 will cause the later to have a strong tendency to dispose itself in an accentuated undulated manner after it is taken out of package 1, which makes its handling by the user difficult.

Thus, since the sutures that take on an as rectilinear configuration as possible when they are taken out of the corresponding package and left at ret are advantageous in the technique, the applicant has carried out various researches, the results of which show that the sutures wound in a non-crossed manner, that is to say, in a circular or oval manner, in the respective packages tend to dispose themselves in a substantially less undulated manner after they are taken out of said packages.

On the other hand, due to the already mentioned tendency to centrifugal expansion of the sutures wound in a circular or oval manner, if the latter are retained in packages made in accordance with the teaching of the prior art, there will be the risk of one or more portions of the sutures being unduly caught by the second tongue 25 when the latter is inserted in the second slot 26, making the removal of suture 12 from package 1 difficult. Also as already mentioned, there is a greater centrifugal expansion in sutures made of synthetic material, especially those that are monofilamentary and made of polymers.

According to the present invention, this problem is solved through an improved folding package, the exemplifying embodiment of which is shown in its open position, that is to say, unfolded and disposed in a planar manner, in FIG. 7 and generically indicated by number 100.

Due to the innovative conception of package 100, a suture wound in an oval manner can be retained in it without the risk of undue retentions when it is taken out.

In addition, as already mentioned, this embodiment of folding package 100 is particularly suitable for storing sutures provided with a great elastic memory, as for instance those made of a monofilamentary polymeric material, for example nylon, polyester, polyethylene and polipropylene. Package 100 comprises first rectangular retaining panel 101 connected respectively and foldingly by its longer longitudinal edges to a second retaining panel 102 and to a first locking panel 103, both of them rectangular as well. The latter panel 103 is also foldingly connected, always by its longitudinal edge, to a second locking panel 104.

According to a preferred embodiment of the invention, this second locking panel 104 has a reduced longitudinal dimension as compared with the corresponding dimension of the other panels 101–103.

Package 100 further includes first and second auxiliary retaining panels 105 and 106, approximately square and foldingly joined to the shorter transverse edges of the first retaining panel 101.

Panels 101 through 106, which form package 100, are preferably made of cardboard of any are weight, so that the final cost of the package can be kept at minimal levels. Of course, such panels can also be made of plastic, metallic (aluminum) films or of any other flexible material. Besides, it is pointed out that the existence of the second auxiliary retaining panel 106 is optional, so it can be eliminated in order to reduce the final cost of the package further.

In the embodiment of package 100 now described, two bores 110 are provided in the first retaining panel 101, through which respective pins 111 are introduced, the function of which is to facilitate the manual winding of a suture 115 having a needle 116 fixed at one of its ends. Optionally, suture 115 can have a needle fixed at each of its ends or even no needle at all. In addition, package 100 can contain more than one suture 115.

According to this invention and as illustrated in FIG. 7, suture 115 is wound in a non-crossed manner around pins 111, so that the turns of the suture can take on a substantially oval configuration, as they expand centrifugally when released. As already mentioned, this centrifugal expansion results form the elastic memory of suture 115, which is especially great when the latter is made of a monofilamentary polymeric material.

As already mentioned too, suture 115 provided with an elastic memory, which are wound and stored in an oval or circular (non-crossed) manner tend to dispose themselves in a quite less undulated manner when taken out of the respective packages 100, unlike sutures wound in a crossed manner. This tendency render the sutures kept in packages 200 made in accordance with the teachings of his invention much easier to use, because they dispose themselves in a substantially rectilinear manner after being taken out of the respective packages 100.

The process of folding panels 101–106 in order to close and form the definitive package 100 is carried out in an analogous manner as described with respect to package 1 of the prior art and illustrated in accompanying FIGS. 1 through 6. Thus, when package 100 is closed, needle 116 is advantageously kept in a compartment separated from suture 115, which prevents it from being accidentally cut and the edges of needle 116 from being damaged.

It is generally advantageous to fix a retaining body 117 on the front face of the first retaining panel, in which needle 116 can be introduced for a better immobilization. According to the preferred embodiment, this body 117 is tridimentional and made of polymeric foam, but it can be made of cardboard or any other resilient material as well.

Package 100 further includes a first locking device made up of first tongue 120, provided at the free longitudinal edge of the second retaining panel 102 and a first slot 212 capable of receiving the first tongue 120 and disposed at the edge joining the first retaining panel 101 with the first locking panel 103. The function of this first locking device 120,121 is to maintain the second retaining panel 102 folded over the first retaining panel 101 with suture 115 and the second auxiliary retaining panel 106 between them, just as illustrated in FIG. 3.

According to an optional embodiment, the second auxiliary retaining panel 106 can be folded over the second retaining panel 102, which in turn is folded over the first retaining panel 101 and suture 115.

According to the invention, a second locking device is provided, made up of a second tongue 130 located at the free edge of the second locking panel 104 and whose symmetry axis is parallel to both the joining lines between the retaining panel and the locking panel 101–104 and the longitudinal axis of package 100 when closed.

Said second locking device further comprises a second slot 131 disposed substantially in the center of the first retaining panel 101 between bores 110 and transversely to the longitudinal axis of said first panel 101.

The second locking device 130,131 serves to immobilize the second locking panel 104 on the back face of the first retaining panel 101, in an analogous way as illustrated in FIG. 6, maintaining package 100 in its folded condition. In this way, the second locking device 130,131 causes the existence of the first above-mentioned locking device 120, 121 to be only optional.

According to the present invention and unlike the prior art, there is no possibility of the second tongue 130 wrongly catching a portion of suture 115 when it goes into the second slot 131, because, since the suture 115 is advantageously wound in an oval manner over the first retaining panel 101, no turn or portion of the suture 115 will dispose itself in the central region of this panel 101 due to the tendency to centrifugal expansion of its turns in the direction of the edges of said panel 101, caused by the elastic memory of the material that usually composes suture 115.

Although the second tongue 130 is preferably arranged with its symmetry axis parallel to the longitudinal axis of package 100 when closed, with the second slot 131 transverse to this axis, a folding package 100 having a second tongue whose symmetry axis is perpendicular or even disposed diagonally with respect to said axis of package 100, the second slot being positioned accordingly, is also in the scope of this invention.

In addition, the second locking panel 104 may be eliminated. In this case, the second tongue 130 should be disposed at the free edge of the first locking panel 103, always with the respective symmetry axis parallel to the axis of package 100.

As illustrated in FIG. 7, the first locking panel 103 preferably has a weakened line 135, which can easily be torn so that a portion of this first locking panel 103 and subsequently the first auxiliary retaining panel 105 can be raised by the user. In this way, the access to suture 115 and needle 116is facilitated.

In addition, the back face of the first locking panel 103, which faces the outside after package 100 is closed can contain information about suture 115 and needle 116 (diameter, length, etc.).

FIG. 8 refers to a second embodiment of this invention, which is suited for retaining surgical sutures provided with any degree of elastic memory.

As illustrated, package 200 has several portions identical to those that compose package 100 illustrated in FIG. 7. In this way, these portions will be designated in FIG. 8 with the same reference numbers of FIG. 7.

As can be seen, the difference between package 200 and that indicated by number 100 in FIG. 7 and described above lies in the number and the arrangement of bores 201,202 in the first retaining panel 101.

In order for package 200 to store surgical sutures provided with any degree of elastic memory, without there being the risk of a portion thereof being unduly retained by the second locking device 130,131, the turns of suture 115 have to be originally disposed along a substantially circular or oval path. This is because in suture made of materials that have a lower degree of elastic memory, as for instance those made of a material of either animal or vegetable origin ("cat gut", silk, cotton, etc.) or a woven polymeric material (nylon, polyester, polyethylene, polypropilene, etc.), the tendency to centrifugal expansion after the winding can be insufficient for ensuring that the turns of suture 115 will displace as far as the edges of the first retaining panel 101, leaving the central portion of said panel 101 totally free, where the second slot 131 is disposed.

Thus, according to the embodiment illustrated in FIG. 8, said bores 201,202 are arranged along substantially semicircular paths in respective first and second groups adjacent the shorter transverse edges of the first retaining panel 101. In this way, during the step of winding suture 115, a plurality of pins 111 go through bores 201,202 and facilitate the arrangement of the turns of future 115 along an oval path that is already adjacent the edges of the first retaining panel 101, independently of a centrifugal expansion of the turns of suture 115.

Preferably at least 3 (three) bores 201,202 are provided in each of said first and second groups, respectively arranged in accordance with semicircular path, so that suture 115 will be wound without any accentuated folds around pins 111.

Besides, the diameter of the semicircles formed by bores 201,202 still according to a preferred embodiment is only slightly smaller than the width of the first retaining panel 101.

It should be noted that the folding packages for surgical products described above are but preferred embodiments of the present invention, the real scope of which is defined by the accompanying claims.

We claim:

1. A folding package for surgical products (100,200), particularly adapted for retaining a surgical suture (115,116), characterized by comprising:

first and second elongated retaining panels (101,102) foldingly joined to each other by their longitudinal edges, the suture (115,116) being wound in a non-crossed manner over the first retaining panel (1010);

a first auxiliary retaining panel (105) foldingly joined to a transverse edge of the fist retaining panel (101);

a first elongated locking panel (103), the longitudinal edge of which is foldingly joined to the longitudinal edge of the first retaining panel (101) opposite the second retaining panel (102), the first locking panel (103) having a substantially transverse weakened line (135) and, bores (201, 202) in the first retaining panel (101), which are arranged along substantially semicircular paths, through which pins (111) that facilitate the winding of the suture (115,116) can pass.

2. A package (100,200) in accordance with claim 1, characterized in that the retaining panels (101, 102) and the first locking panel (103) are rectangular; and by further comprising:

a second rectangular locking panel (104) foldingly joined to the longitudinal edge of the first locking panel (103); and a locking device of the tongue-slot type (130, 131), the respective slot (131) being disposed in a transversely median position in the first retaining panel (101), and the respective tongue (130) being disposed at the free edge of the second locking panel (104), with its symmetry axis substantially parallel to the longitudinal edges of the retaining panels (101, 102) and of the first locking panel (103).

3. A folding package for surgical products (100,200), particularly adapted for retaining a surgical suture (115,116), characterized by comprising:

first and second retaining panels (101,102) foldingly joined to each other by their edges, the suture (115,116) being wound in a non-crossed manner over the first retaining panel (1010:

a first locking panel (103), the edge of which is foldingly joined to the edge of the first retaining panel (101) opposite the second retaining panel (102); and a locking device of the tongue-slot type (130,131), the slot (131) being disposed in a transversely median position of the first retaining panel (1010 and, a second locking panel (104) foldingly joined to the longitudinal edge of the first locking panel (103); the tongue (130) of the locking device being disposed at the free edge of this second locking panel (104) substantially parallel to the longitudinal edges of the retaining panels (101, 102) and of the first locking panel (103) wherein the slot (131) being transversely disposed with respect to the longitudinal axis of the first retaining panel (101).

4. A package (100,200) in accordance with claim 3, characterized in that the second locking panel (104) has a reduced longitudinal dimension with respect to the longitudinal dimensions of the retaining panels (101, 102) and of the first locking panel (103).

5. A folding package for surgical products (100,200), particularly adapted for retaining a surgical suture (115,116), characterized by comprising:

first and second retaining panels (101,102) foldingly joined to each other by their edges, the first retaining panel (101) having bores (201,202) arranged along substantially semicircular paths, through which pins (111) that facilitate the winding of the suture (115,116) in a non-crossed manner can pass;

first and second locking panels (103,104) foldingly joined to each other, the first locking panel (103) being rectangular and foldingly joined by its longitudinal edge to the longitudinal edge of the first retaining panel (101) opposite the second retaining panel (102); and a locking device of the tongue-slot type (130,131), the respective slot (131) being disposed in a transversely median position in the first retaining panel (101), and the respective tongue (130) being disposed at the free edge of the second locking panel (104) substantially parallel to the longitudinal edge of the retaining panels (101,102) and of the first locking panel (103).

6. A package (100,200) in accordance with claim 5 characterized in that the slot (131) is substantially transverse to the longitudinal axis of the first retaining panel (101).

* * * * *

UNITED STATES PATENT AND TRADEMARK OFFICE
CERTIFICATE OF CORRECTION

PATENT NO. : 5,533,611
DATED : July 9, 1996
INVENTOR(S) : Marcos A. Bordighon
Jose L. L. Januzelli It is certified that error appears in the above-indentified patent and that said Letters Patent is hereby corrected as shown below:

Column 7 - Line 55 - "fist" should be "first"

Signed and Sealed this

Fifteenth Day of July, 1997

Attest:

BRUCE LEHMAN

*Attesting Officer*    Commissioner of Patents and Trademarks